United States Patent [19]

Trauffer et al.

[11] Patent Number: 5,347,003

[45] Date of Patent: Sep. 13, 1994

[54] METHODS FOR REGENERATING A SULFUR SCAVENGING COMPOUND FROM A PRODUCT OF A SULFUR SCAVENGING REACTION

[75] Inventors: Edward A. Trauffer, Glenside; Robert D. Evans, Warminster, both of Pa.

[73] Assignee: Quaker Chemical Corporation, Wilmington, Del.

[21] Appl. No.: 26,891

[22] Filed: Mar. 5, 1993

[51] Int. Cl.$^5$ .................. C07C 211/09; C07D 251/04
[52] U.S. Cl. ......................................... 544/8; 544/180; 544/215; 544/358; 544/404; 546/184; 548/215; 548/300.1; 548/335.1; 564/8; 564/437; 564/457; 564/461; 564/487; 564/506; 564/511; 423/226; 423/228
[58] Field of Search ............... 544/180, 215, 358, 404, 544/8; 546/184; 548/215, 335.1, 300.1; 564/8, 437, 457, 461, 506, 511, 487; 423/226, 228

[56] References Cited

U.S. PATENT DOCUMENTS

| | | | |
|---|---|---|---|
| 2,776,870 | 1/1957 | Fischer | 23/2 |
| 4,112,051 | 9/1978 | Sartori et al. | 423/223 |
| 4,624,838 | 11/1986 | Pan et al. | 423/226 |
| 4,647,397 | 3/1987 | Starkston et al. | 252/189 |
| 4,775,519 | 10/1988 | Yit Nieh | 423/226 |
| 4,978,512 | 12/1990 | Dillon | 423/226 |
| 5,128,049 | 7/1992 | Gatlin | 210/752 |

FOREIGN PATENT DOCUMENTS 2103645 2/1983 United Kingdom.

*Primary Examiner*—Richard L. Raymond
*Attorney, Agent, or Firm*—Panitch Schwarze Jacobs & Nadel

[57] ABSTRACT

Methods are provided whereby an N-C-N compound is regenerated from a product of a sulfur scavenging reaction, in which said N-C-N compound removes a sulfur atom from a sulfur compound, to form the original N-C-N compound. The N-C-N compound is represented by the formula (I):

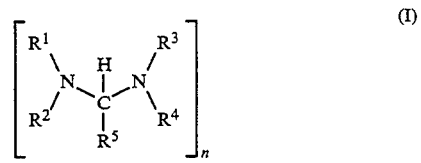

The product includes a hetero compound having sulfur, carbon and nitrogen atoms in its backbone. In one embodiment, the product is mixed with (1) a nitrogen compound represented by the formula (II):

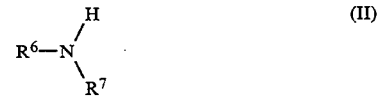

and (2) an alkaline compound selected from alkali metal, alkaline earth metal and transition metal compounds, to form a solution, slurry or dispersion. The hetero compound is reacted with the nitrogen compound in the presence of the alkaline compound, such that a sulfur atom of the hetero compound is replaced by a nitrogen atom of the nitrogen compound. If necessary, the pH of the solution may be adjusted to about 8 to about 13 to facilitate the reaction. In alternative embodiments, the product also includes an amine complex. The nitrogen atom being substituted for the sulfur atom in the hetero compound may be obtained from either the nitrogen compound or the amine complex.

17 Claims, No Drawings

METHODS FOR REGENERATING A SULFUR SCAVENGING COMPOUND FROM A PRODUCT OF A SULFUR SCAVENGING REACTION

FIELD OF THE INVENTION

The present invention relates to methods for regenerating a sulfur scavenging compound from a product of a sulfur scavenging reaction and, more particularly, to regenerating an N-C-N compound from a product of a sulfur scavenging reaction that has typically been difficult or expensive to regenerate.

BACKGROUND OF THE INVENTION

Hydrogen sulfide and mercaptans are toxic, corrosive and malodorous compounds. Each may be found in a variety of liquid and gaseous media such as natural gas, petroleum, refinery gas streams, carbon dioxide, hydrogen, coal gas streams, gas streams from viscose rayon production, tars and asphalt, shale gas, coke oven gases, ammonia synthesis gas, rubber vulcanization streams, gases from sulfurization plants, turpentine production, pulp and paper mill effluent, sewage, brine drilling mud, land fills, phosphoric acid production gas streams and other industrial gas streams and effluents. They are also found in the tail gases and liquids of some hydrogen sulfide scrubbing processes such as Claus plants and amine scrubbing units. Such sulfur compounds include hydrogen sulfide, allyl thiol, propane thiol, benzyl thiol, crotyl thiol, ethane thiol, thiocresol and thiophenol.

Hydrogen sulfide is an undesirable contaminant which is highly toxic, corrosive and has an objectionable odor. The release of hydrogen sulfide into the environment is strictly controlled by the Environmental Protection Agency and Department of Environmental Resources, as well as by other regulatory agencies throughout the world. Hydrogen sulfide and mercaptans not only have an offensive odor, but have also been linked to the formation of acid rain.

Methods for removing hydrogen sulfide and/or mercaptans may be generally classified as regenerative and non-regenerative. Regenerative processes are generally more desirable because waste products are recycled. By regenerating sulfur scavenging compounds and thereby recycling the waste products, the cost, both economically and environmentally, of replenishing spent chemicals in the process and disposing of the waste products is lessened or eliminated. However, typical prior art regenerative processes often require expensive processing equipment and high energy input.

Various amines and alkanomines, which may be regenerated, have been used to remove acids, such as hydrogen sulfide, from gas streams. U.S. Pat. No. 2,776,870 discloses that aqueous amines and alkanolamines are useful for removing acids from a gaseous mixture. Hydrogen sulfide may be selectively removed from gas streams containing carbon dioxide by use of triethanolamine or methyldiethanolamine.

British Published Patent Specification No. 2103645 discloses that hydrogen sulfide and carbon dioxide may be removed from a gas mixture by contacting the mixture with a solvent comprising a tertiary amine and a physical absorbent. Suitable physical absorbents include N-methylpyrrolidone and sulfolane.

U.S. Pat. No. 4,112,051 discloses a process for removing acidic gases from a gaseous mixture with an amine-solvent liquid absorbent comprising (1) an amine comprised of at least about 50 mole percent of a sterically hindered amine; and (2) a solvent for the amine mixture which is also a physical absorbent for the acidic gases. Suitable sterically hindered amines include various piperidine compounds. Suitable solvents include sulfones and pyrrolidone and piperidone compounds, to name a few.

U.S. Pat. No. 4,978,512 discloses methods for reducing the levels of hydrogen sulfide and organic sulfides in a hydrocarbon stream by contacting the stream with a composition comprising a reaction product of a lower alkanolamine with a lower aldehyde. Suitable reaction products include mixtures of triazine and bisoxazolidine compounds.

U.S. Pat. No. 4,647,397 discloses a process and composition for removing hydrogen sulfide and similar sulfides from a gas stream. The gas stream is contacted with a substituted aromatic nitrile having an electron-attracting substitute on the aromatic ring at least as strong as halogen and an organic tertiary amine in an inert organic solvent, such as N-methyl-2-pyrrolidone. The spent contacting solution may be regenerated by heating the solution above the decomposition temperature of the reaction products to separate the sulfides from the liquid phase absorbent solution.

U.S. Pat. No. 4,775,519 discloses a continuous process for removing acid gas components from a gas stream by countercurrently contacting the stream with an aqueous solution of a mixture of N-methyldiethanolamine (MDEA) with imidazole or a methyl substituted imidazole. The gas is deabsorbed from the MDEA and the imidazole by reducing the pressure and causing the gas to flash.

U.S. Pat. No. 4,624,838 discloses a process for removing acid gases from a gaseous stream by contacting the stream with an aqueous scrubbing solution containing a hetero nitrogen compound comprising either a five- or six- membered ring having a pKa no greater than about 8. Preferred hetero nitrogen compounds include imidazole and piperazine compounds.

U.S. Pat. No. 5,128,049 discloses a method for reducing the hydrogen sulfide content of hydrocarbon-containing fluids and aqueous solutions by injections of a dilute solution of a scavenging agent. Suitable scavenging agents include hexahydro-1,3,5-tris(2-hydroxyethyl)-S-triazine and various other compounds.

There is a long-felt need in the art for a method for regenerating sulfur scavenging compounds. Regenerating such compounds is not only environmentally desirable but is cost efficient and may reduce or eliminate the need for expensive processing equipment. In addition, since the scavenging compounds are regenerated, the need for purchasing replacement scavenging compound is reduced or eliminated.

DEFINITIONS

As used herein, the phrase "hetero compound" is defined to mean a cyclic, linear or branched compound in which one or more atoms of the backbone is an element other than carbon, particularly at least nitrogen and sulfur and possibly oxygen.

As used herein, the phrase "heterocyclic compound" is defined as a compound having a closed ring structure in which one or more atoms in the backbone of the ring is an element other than carbon, particularly at least nitrogen and sulfur and possible oxygen. The heterocyclic compound may have straight, branched or cyclic substituents.

SUMMARY OF THE INVENTION

Briefly stated, one aspect of the present method is a method for regenerating an N-C-N compound from a product of a sulfur scavenging reaction in which the N-C-N compound removes a sulfur atom from a sulfur compound. The N-C-N compound is represented by the following formula (I):

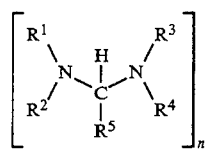
(I)

where n is an integer of 1 to 100. Each of $R^1$, $R^2$, $R^3$, $R^4$, and $R^5$ is independently selected from the group consisting of: (i) hydrogen; (ii) a substituted or unsubstituted, saturated or unsaturated, linear, branched or cyclic hydrocarbon chain of 1 to 20 carbons; (iii) a substituted or unsubstituted, saturated or unsaturated, linear, branched or cyclic hydrocarbon chain of 1 to 20 carbons comprising at least one heteroatom selected from the group consisting of nitrogen, oxygen, sulfur and halogen; (iv) a substituted or unsubstituted polymeric chain; and (v) a direct bond to any other of $R^1$, $R^2$, $R^3$, $R^4$, and $R^5$. The product comprises a hetero compound having sulfur, carbon and nitrogen atoms in its backbone. According to the method, the product is mixed with: (a) a nitrogen compound represented by the formula (II):

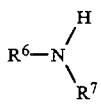
(II)

where each of $R^6$ and $R^7$ are independently selected from the group consisting of (i) hydrogen; (ii) a substituted or unsubstituted, saturated or unsaturated, linear, branched or cyclic hydrocarbon chain of 1 to 20 carbons; (iii) a substituted or unsubstituted, saturated or unsaturated, linear, branched or cyclic hydrocarbon chain of 1 to 20 carbons comprising at least one heteroatom selected from the group consisting of nitrogen, oxygen, sulfur and halogen; (iv) a substituted or unsubstituted polymeric chain; and salts thereof; and (a) an alkaline compound (base) selected from the group consisting of an alkali metal compound, an alkaline earth metal compound and a transition metal compound, to form a solution, slurry or dispersion. The hetero compound is reacted in this solution with the nitrogen compound in the presence of the alkaline compound. By this method, the sulfur atom of the hetero compound is replaced by a nitrogen atom of the nitrogen compound. If necessary, the pH of the solution is adjusted to about 8 to about 13.

In another embodiment of this invention, the product comprises a hetero compound and an amine. In this embodiment, addition of the nitrogen compound is omitted, since the sulfur atom of the hetero compound is replaced by the nitrogen atom of the amine compound.

In yet another embodiment of the present invention, the product comprises both the hetero compound and an amine complex. The nitrogen compound is added in this method, and the sulfur atom of the hetero compound is replaced by a nitrogen atom of either the nitrogen compound or the amine complex.

DESCRIPTION OF THE PREFERRED EMBODIMENTS

The present methods for regenerating an N-C-N compound from a product of a sulfur scavenging reaction are both simple and inexpensive. These methods are useful both for batch processes and continuous processes to permit recirculation of regenerated sulfur scavenging compounds. In the present methods, the need for complicated processing machinery, the purchase of additional sulfur scavenging compounds and the disposal of valuable hetero compounds as waste products are reduced or eliminated.

The present method may be used for regenerating an N-C-N compound from a product of a sulfur scavenging reaction. In the sulfur scavenging reaction, the N-C-N compound removes a sulfur atom from a sulfur compound. The N-C-N compound is represented by the formula (I):

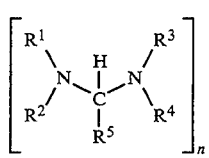
(I)

where n is an integer of 1 to 100 and preferably 1 to 20.

Each of $R^1$, $R^2$, $R^3$, $R^4$, and $R^5$ is independently selected from (i) hydrogen; (ii) a substituted or unsubstituted, saturated or unsaturated, linear, branched or cyclic hydrocarbon chain of 1 to 20 carbons; (iii) a substituted or unsubstituted, saturated or unsaturated, linear, branched or cyclic hydrocarbon chain of 1 to 20 carbons comprising at least one heteroatom selected from nitrogen, oxygen, sulfur or halogen; (iv) a substituted or unsubstituted polymeric chain; and (v) a direct bond to any other of $R^1$, $R^2$, $R^3$, $R^4$, and $R^5$. Preferably $R^1$ is linked to $R^3$ to form a heterocyclic ring.

Examples of N-C-N compounds which may be regenerated in the present method include various triazines, such as 1,3,5-tri(2-hydroxyethyl)hexahydro-S-triazine, and trimethyltriazine, bisoxazolidines, such as N,N-methylene bisoxazolidine, piperidines, piperazines, imidazoles, diazathianes, amines, such as methyldiethanolamine, bis(dibutylamino)methane and bis(di-2-hydroxyethylamino)methane, bis(morpholino)methane and 1,3,6,8-tricyclotetraaza[4,4,1,1$^{3,8}$]-dodecane.

The product comprises a hetero compound formed as a result of a sulfur scavenging reaction. The hetero compound has carbon and nitrogen atoms, and optionally may have oxygen or other heteroatoms, in its backbone. Examples of hetero compounds which may be converted in the present methods include dithiazines and thiazolidines, to name a few.

In addition to the hetero compound, the sulfur scavenging reaction may also yield as a product an amine complex, such as an amine salt with hydrogen sulfide or mercaptan. Examples of such amine salts include those having the general formula $R-NH_3^+\ SH^-$ where R is an alkanol group for example $HOCH_2CH_2NH_3^+SH^-$. The amine complex may be separated from the hetero compound prior to the regeneration reaction or it may be included in the regeneration. If included, the amine complex is a source of nitrogen atoms for replacing the sulfur atom of the hetero compound. By including part or all of the amine complex in the regeneration reaction, the cost of separating the hetero compound from the amine complex prior to regeneration is reduced or eliminated. Also, the amount of nitrogen compound added to the hetero compound for conducting the regeneration reaction may be reduced or eliminated.

An example of a typical sulfur scavenging reaction is set forth generally below in reaction equation (III), in which a triazine reacts with hydrogen sulfide to yield a dithiazine and a primary amine complex.

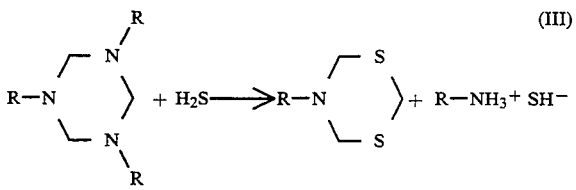

The nitrogen compound is represented by the formula (II):

where each of $R^6$ and $R^7$ are independently selected from (i) hydrogen; (ii) a substituted or unsubstituted, saturated or unsaturated, linear, branched or cyclic hydrocarbon chain of 1 to 20 carbons; (iii) a substituted or unsubstituted, saturated or unsaturated, linear, branched or cyclic hydrocarbon chain of 1 to 20 carbons comprising a heteroatom selected from nitrogen, oxygen, sulfur and a halogen; (iv) a substituted or unsubstituted polymeric chain; and salts thereof. Examples of such nitrogen compounds include ammonia, ethanolamine, diethanolamine, methylamine, cyclohexylamine, ethylene diamine, morpholine and thiomorpholine.

Generally, about 0.25 to about 4 molar equivalents of the nitrogen compound and/or amine complex may be used in the present methods for each equivalent of hetero compound. As presently preferred, about 0.5 to about 2 molar equivalents and, more preferably, about 0.75 to about 1.5 molar equivalents of nitrogen compound and/or amine complex may be used for each equivalent of hetero compound.

The reaction by which the sulfur atom of the hetero compound is replaced by a nitrogen atom is carried out in the presence of an alkaline compound (base) selected from alkali metal, alkaline earth metal and transition metal compounds. Examples of alkaline compounds which are useful in the present method include sodium hydroxide, potassium hydroxide, calcium hydroxide, calcium oxide, magnesium oxide, sodium carbonate, sodium bicarbonate and calcium carbonate. Generally, the alkaline compound has a pH greater than the pH of the product and, in those embodiments in which the nitrogen compound is mixed with the product, greater than the mixture of the product and the nitrogen compound.

Generally, about 0.5 to about 8 equivalents of the alkaline compound are mixed with one equivalent of the hetero compound. Preferably, about 0.5 equivalents to about 4 equivalents of the alkaline compound are used per equivalent of hetero compound and, more preferably, about one to about two equivalents of alkaline compound. Generally, if lower quantities of the alkaline compound are used, some unregenerated product will remain in the solution. In contrast, an excess of alkaline compound is not believed to negatively effect the regeneration reaction, except that additional neutralization may be necessary.

For example, if the alkaline compound is NaOH, the sulfur atoms removed from the hetero compound bond with the sodium atoms from the NaOH to form sodium compounds such as sodium sulfide and/or sodium hydrosulfide, for example. The sodium compound(s) may be separated from the regenerated scavenging compound, if desired, by any method well-known to those of ordinary skill in the art, such as by solvent extraction of the N-C-N compound with a solvent such as methylene chloride or by distillation. However, the sodium compound need not be separated from the regenerated sulfur scavenging N-C-N compound, but may be included with the scavenging N-C-N compound recycled to the scavenging process.

The reaction for replacing the sulfur atom of the hetero compound with a nitrogen atom may be carried out in the presence of a solvent. Solvents may be used to adjust the viscosity or facilitate mixing of the reaction components. Suitable solvents include water, methanol, ethanol and ethylene glycol, as well as any other polar solvents in which the hetero compound and the N-C-N compound are both sufficiently soluble.

The percentage of solvent generally ranges from 0 to about 90 wt %. Preferably, the percentage of solvent is about 25 to about 75 wt % and, more preferably, about 40 to about 60 wt %. Typically, the solvent is mixed with the product and nitrogen compound prior to adding the alkaline compound, although the mixing method may vary depending upon the components selected.

According to the present method, the hetero compound product is mixed with the nitrogen compound and the alkaline compound to form a solution, dispersion or slurry. In an alternative embodiment of the present method, the product also includes the amine complex. In this alternative embodiment, the product, comprising the hetero compound and amine complex, is mixed with the alkaline compound to form the solution. The amine complex provides the nitrogen atoms which replace the sulfur atoms of the hetero compound.

In another alternative embodiment, the product, comprising the hetero compound and amine complex, is mixed with the alkaline compound and the nitrogen compound. Either or both of the amine complex and the nitrogen compound provide the nitrogen atoms for replacing the sulfur atom of the hetero compound.

The product and nitrogen compound may be mixed together prior to mixing with the alkaline compound or all of the components may be mixed together to form a solution. The components may be mixed, for example, in a typical reaction vessel for a batch process or by in-line injection in a recirculating system.

Preferably, the replacement of the sulfur atom of the hetero compound by a nitrogen atom of the nitrogen compound or amine complex is carried out at a temperature of about 25° to about 105° C. It is believed that elevated temperatures will increase the rate of reaction.

According to the present method, the pH of the resulting solution is adjusted to about 8 to about 13 and, more preferably, about 9 to about 11. The pH of the solution may be adjusted by the addition of a mineral acid, such as hydrochloric acid, sulfuric acid, phosphoric acid or nitric acid. The mineral acid is added to neutralize excess alkaline compound and lower the pH of the solution to facilitate regeneration of the N-C-N compound and reduce the likelihood of formation of undesirable by-products. If the N-C-N compound is reacted with essentially pure hydrogen sulfide, e.g., about 90 to 100 wt %, acid adjustment is generally not necessary because the pH of the solution is low enough to drive the regeneration reaction essentially to completion.

The present method will now be illustrated in more detail by reference to the following, specific, non-limiting examples.

EXAMPLE 1

Seventy (70) grams of an aqueous solution of 7.3 wt % 1,3,5-tri(2-hydroxyethyl)hexahydro-S-triazine ("triazine compound"), which is commercially available from Quaker Chemical Co. of Conshohocken, Pa., a well-known sulfur scavenging compound, was reacted with 99.5% hydrogen sulfide to completion (206 mmol hydrogen sulfide was scavenged). Complete reaction was verified by 13 C NMR. Ten milliliters of a 6N aqueous solution of sodium hydroxide was added to the product of the sulfur scavenging reaction and the resulting reaction mixture was heated to 70° C. for one hour. Acid neutralization of the reacted mixture was not required since 99.5 wt % hydrogen sulfide was used in the sulfur scavenging reaction. At the end of one hour, the regeneration of the triazine compound was confirmed by 13 C NMR. The regenerated triazine compound was again reacted with 99.5 wt % hydrogen sulfide to completion. The reaction of the regenerated triazine compound with hydrogen sulfide followed by regeneration of the triazine compound was repeated for ten cycles according to the present method. No diminishment of the sulfur scavenging efficiency of the regenerated triazine compound was observed.

EXAMPLE 2

Ten (10) grams of a 25 wt % solution of 1,3,6,8-tricyclotetraaza[4,4,1,1$^{3,8}$]dodecane was reacted to completion with 99.5 wt % hydrogen sulfide in the manner set forth in Example 1. The product produced a gummy residue that clogged the scrubbing test equipment. The product showed no signs of the unreacted tetraaaza compound. The product was then reacted with 10 milliliters of a 6N aqueous sodium hydroxide solution at 80° C. for one hour. After 30 minutes, the appearance of the reaction mixture returned to that of the unreacted sulfur scavenging compound. Acid neutralization of the mixture was not required since 99.5 wt % hydrogen sulfide was used in the sulfur scavenging reaction. A 13 C NMR analysis of the reaction product showed complete regeneration of the 1,3,6,8-tricyclotetraaza[4,4,1,1$^{3,8}$]dodecane sulfur scavenging compound.

Ten (10) grams of a 43 wt % aqueous solution of the triazine compound of Example 1 was reacted with 2,000 ppm (parts per million) hydrogen sulfide in methanol. Upon completion of the reaction, the resulting dithiazine and ethanolamine-hydrosulfide salt were separated. The dithiazine was reacted with a 10 molar excess of a 6N aqueous solution of sodium hydroxide at 80° C for two hours. Analysis by 13 C NMR of the resulting product showed formation of 1,3,5-tri(2-hydroxyethyl)-hexahydro-S-triazine and approximately 10 wt % of an unidentified sulfur-containing compound. The ethanolamine-hydrosulfide salt was separately reacted with an excess of sodium hydroxide at 80° C. for two hours. Analysis of the resulting product showed that uncomplexed ethanolamine was formed. Acid neutralization was not required in either of these reactions since 99.5 wt % hydrogen sulfide was used in the sulfur scavenging reaction.

EXAMPLE 4

Ten (10) grams of a 43 wt % aqueous solution of the triazine compound of Example 1 was reacted with 99.5 wt % hydrogen sulfide to completion. The resulting 5,6-dihydro-5-(2-hydroxyethyl)-4H-1,3,5-dithiazine was isolated and reacted with three molar equivalents of a 6N sodium hydroxide aqueous solution in an excess of ethanolamine at 70° C. Acid neutralization was not required since 99.5 wt % hydrogen sulfide was used in the sulfur scavenging reaction. The reaction product consisted solely of 1,3,5-tri(2-hydroxyethyl)hexahydro-S-triazine, which was the original sulfur scavenging compound.

EXAMPLE 5

Ten (10) grams of a 43 wt % aqueous solution of the triazine compound of Example 1 was reacted to saturation with 99.5 wt % hydrogen sulfide to form 5,6-dihydro-5-(2-hydroxyethyl)-4H-1,3,5-dithiazine and ethanolamine-hydrosulfide. This mixture was reacted with three molar equivalents of sodium hydroxide at 70° C. for 30 minutes. Analysis by 13 C NMR showed that the mixture was completely converted to 1,3,5-tri(2-hydroxyethyl)hexahydro-S-triazine. The regenerated triazine compound was placed in a bubble flask through which 2,000 ppm hydrogen sulfide in methane was passed. The regenerated triazine compound was unable to react with hydrogen sulfide, as evidenced by a complete lack of hydrogen sulfide absorbance. One equivalent of hydrochloric acid was then added to the reaction mixture and the mixture was mixed for 10 minutes at room temperature. The acid-adjusted mixture was again analyzed by 13 C NMR, which confirmed that the mixture contained the regenerated triazine compound. The acid-adjusted mixture was again placed in a bubble flask through which 2,000 ppm hydrogen sulfide in methane was bubbled. The acid-adjusted regenerated triazine was found to react normally with the hydrogen sulfide.

The foregoing examples clearly show that N-C-N compounds may be regenerated from the product(s) of a sulfur scavenging reaction, in which the N-C-N compound removes a sulfur atom from a sulfur compound, such as hydrogen sulfide or a mercaptan, according to the present methods. The hetero compound product of the sulfur scavenging reaction may be separated from other products of the reaction prior to regeneration according to the present method. Alternatively, the product may comprise both a hetero compound and an amine complex, from which nitrogen atoms are obtained to convert the hetero compound to the starting sulfur scavenging compound by one of the present methods. In another embodiment, a hetero compound and an amine complex may be mixed with a nitrogen compound to convert the hetero compound to the starting sulfur scavenging compound. By adjusting the pH of the reaction mixture, regeneration of the sulfur scavenging compound may be facilitated.

The present methods easily convert hetero compound products of sulfur scavenging reactions without the need for costly regeneration equipment typically required for oxygen and heat regeneration processes.

By regenerating the N-C-N compounds, the need for purchasing additional scavenging compounds and disposing of the spent hetero compounds as waste is reduced or eliminated.

The present invention may be embodied in other specific forms without departing from the spirit or essential attributes thereof and, accordingly, reference should be made to the appended claims rather than to the foregoing specification as indicated the scope of the invention.

We claim:

1. A method for regenerating an N-C-N compound from a product of a sulfur scavenging reaction in which said N-C-N compound removes a sulfur atom from a sulfur compound, said N-C-N compound being represented by the formula (I):

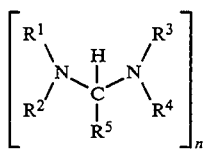

where n is an integer of 1 to 100, and each of $R^1$, $R^2 R^3$, $R^4$, and $R^5$ is independently selected from the group consisting of:
(i) hydrogen;
(ii) a substituted or unsubstituted, saturated or unsaturated, linear, branched or cyclic hydrocarbon chain of 1 to 20 carbons;
(iii) a substituted or unsubstituted, saturated or unsaturated, linear, branched or cyclic hydrocarbon chain of 1 to 20 carbons comprising at least one heteroatom selected from the group consisting of nitrogen, oxygen, sulfur and halogen;
(iv) a substituted or unsubstituted polymeric chain; and
(v) a direct bond to any other of $R^1$, $R^2$, $R^3$, $R^4$, and $R^5$, said product comprising a hetero compound having sulfur, carbon and nitrogen atoms in its backbone, the method comprising the steps of:
(a) mixing said product with:
(1) a nitrogen compound represented by the formula (II):

where each of $R^6$ and $R^7$ are independently selected from the group consisting of:
(i) hydrogen;
(ii) a substituted or unsubstituted, saturated or unsaturated, linear, branched or cyclic hydrocarbon chain of 1 to 20 carbons;
(iii) a substituted or unsubstituted, saturated or unsaturated, linear, branched or cyclic hydrocarbon chain of 1 to 20 carbons comprising at least one heteroatom selected from the group consisting of boron, nitrogen, oxygen, sulfur and halogen; and
(iv) a substituted or unsubstituted polymeric chain; and salts thereof; and
(2) an alkaline compound selected from the group consisting of an alkali metal compound, an alkaline earth metal compound and a transiton metal compound, to form one of a solution, slurry or dispersion;
(b) reacting said hetero compound with said nitrogen compound in the presence of said alkaline compound, such that a sulfur atom of said hetero compound is replaced by a nitrogen atom of said nitrogen compound; and
(c) if necessary, adjusting the pH of said solution to about 8 to about 13.

2. The method according to claim 1, wherein $R^1$ is linked to $R^3$ to form a heterocyclic ring.

3. The method according to claim 1, wherein said N-C-N compound is selected from the group consisting of a triazine, bisoxazolidine, piperidine, piperazine, imidazole, amine and diazathiane.

4. The method according to claim 1, wherein said hetero compound has said sulfur atom located in a $\beta$ position to said nitrogen atom.

5. The method according to claim 1, wherein said hetero compound is selected from the group consisting of a dithiazine and a thiazolidine.

6. The method according to claim 1, wherein said nitrogen compound is selected from the group consisting of ammonia, ethanolamine, diethanolamine, methylamine, cyclohexylamine, ethylene diamine, morpholine and thiomorpholine.

7. The method according to claim 1, wherein said alkaline compound is selected from the group consisting of sodium hydroxide, potassium hydroxide, calcium hydroxide, calcium oxide, magnesium oxide, sodium carbonate, sodium bicarbonate and calcium carbonate.

8. The method according to claim 1, wherein said product further comprises an amine complex.

9. The method according to claim 8, wherein said amine complex comprises an amine salt.

10. The method according to claim 1, wherein said reaction is carried out in the presence of a solvent.

11. The method according to claim 10, wherein said solvent is selected from the group consisting of water, methanol, ethanol, and ethylene glycol.

12. The method according to claim 1, wherein about 0.5 equivalents to about 8 equivalents of said alkaline compound are mixed with 1 equivalent of said hetero compound.

13. The method according to claim 1, wherein the replacement of said sulfur atom of said hetero compound by said nitrogen atom of said nitrogen compound is carried out at a temperature of about 25° C. to about 105° C.

14. The method according to claim 1, wherein the pH of the solution is adjusted by adding a mineral acid to the solution.

15. The method according to claim 14, wherein the mineral acid is selected from the group consisting of hydrochloric acid, sulfuric acid, phosphoric acid and nitric acid.

16. A method for regenerating an N-C-N compound from a product of a sulfur scavenging reaction in which said N-C-N compound removes a sulfur atom from a sulfur compound, said N-C-N compound being represented by the formula (I):

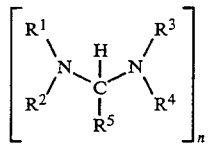

$$\begin{bmatrix} R^1 & H & R^3 \\ \diagdown N & | & N \diagup \\ \diagup & C & \diagdown \\ R^2 & | & R^4 \\ & R^5 & \end{bmatrix}_n \qquad (I)$$

where n is an integer of 1 to 100, and each of $R^1$, $R^2$, $R^3$, $R^4$, and $R^5$ is independently selected from the group consisting of:

(i) hydrogen;
(ii) a substituted or unsubstituted, saturated or unsaturated, linear, branched or cyclic hydrocarbon chain of 1 to 20 carbons;
(iii) a substituted or unsubstituted, saturated or unsaturated, linear, branched or cyclic hydrocarbon chain of 1 to 20 carbons comprising at least one heteroatom selected from the group consisting of nitrogen, oxygen, sulfur and halogen;
(iv) a substituted or unsubstituted polymeric chain; and
(v) a direct bond to any other of $R^1$, $R^2$, $R^3$, $R^4$, and $R^5$, said product comprising a hetero compound and an amine complex, said hetero compound having sulfur, carbon and nitrogen atoms in its backbone, the method comprising the steps of:
(a) mixing said product with an alkaline compound selected from the group consisting of an alkali metal compound, an alkaline earth metal compound and a transition metal compound, to form one of a solution, slurry or dispersion;
(b) reacting said hetero compound with said amine complex in the presence of said alkaline compound, such that a sulfur atom of said hetero compound is replaced by a nitrogen atom of said amine complex; and
(c) if necessary, adjusting the pH of said solution to about 8 to about 13.

17. A method for regenerating an N-C-N compound from a product of a sulfur scavenging reaction in which said N-C-N compound removes a sulfur atom from a sulfur compound, said N-C-N compound being represented by the formula (I):

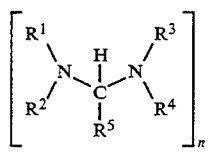

$$\begin{bmatrix} R^1 & H & R^3 \\ \diagdown N & | & N \diagup \\ \diagup & C & \diagdown \\ R^2 & | & R^4 \\ & R^5 & \end{bmatrix}_n \qquad (I)$$

where n is an integer of 1 to 100, and each of $R^1$, $R^2$, $R^3$, $R^4$, and $R^5$ is independently selected from the group consisting of:

(i) hydrogen;
(ii) a substituted or unsubstituted, saturated or unsaturated, linear, branched or cyclic hydrocarbon chain of 1 to 20 carbons;
(iii) a substituted or unsubstituted, saturated or unsaturated, linear, branched or cyclic hydrocarbon chain of 1 to 20 carbons comprising at least one heteroatom selected from the group consisting of nitrogen, oxygen, sulfur and halogen;
(iv) a substituted or unsubstituted polymeric chain; and
(v) a direct bond to any other of $R^1$, $R^2$, $R^3$, $R^4$, and $R^5$, said product comprising a hetero compound and an amine complex, said hetero compound having sulfur, carbon and nitrogen atoms in its backbone, the method comprising the steps of:
(a) mixing said product with:
(1) a nitrogen compound represented by the formula (II):

$$R^6 - N \diagdown_{R^7}^{H} \qquad (II)$$

where each of $R^6$ and $R^7$ are independently selected from the group consisting of:
(i) hydrogen;
(ii) a substituted or unsubstituted, saturated or unsaturated, linear, branched or cyclic hydrocarbon chain of 1 to 20 carbons;
(iii) a substituted or unsubstituted, saturated or unsaturated, linear, branched or cyclic hydrocarbon chain of 1 to 20 carbons comprising at least one heteroatom selected from the group consisting of boron, nitrogen, oxygen, sulfur and halogen; and
(iv) a substituted or unsubstituted polymeric chain; and salts thereof; and
(2) an alkaline compound selected from the group consisting of an alkali metal compound, an alkaline earth metal compound and a transition metal compound to form one of a solution, slurry or dispersion;
(b) reacting said hetero compound with at least one of said amine complex and said nitrogen compound in the presence of said alkaline compound, such that a sulfur atom of said hetero compound is replaced by a nitrogen atom selected from the group consisting of said amine complex and said nitrogen compound; and
(c) if necessary, adjusting the pH of said solution to about 8 to about 13.

* * * * *